(12) United States Patent
Aoki et al.

(10) Patent No.: US 8,580,760 B2
(45) Date of Patent: Nov. 12, 2013

(54) APTAMER CAPABLE OF BINDING TO VIRAL HEMORRHAGIC SEPTICEMIA VIRUS

(76) Inventors: Takashi Aoki, Tokyo (JP); Ikuo Hirono, Tokyo (JP)

(*) Notice: Subject to any disclaimer, the term of this patent is extended or adjusted under 35 U.S.C. 154(b) by 0 days.

(21) Appl. No.: 13/502,154

(22) PCT Filed: Oct. 15, 2010

(86) PCT No.: PCT/JP2010/068115
§ 371 (c)(1),
(2), (4) Date: Jun. 28, 2012

(87) PCT Pub. No.: WO2011/046193
PCT Pub. Date: Apr. 21, 2011

(65) Prior Publication Data
US 2012/0260358 A1    Oct. 11, 2012

(30) Foreign Application Priority Data
Oct. 16, 2009    (JP) .................. 2009-239340

(51) Int. Cl.
*C12N 15/11*    (2006.01)
*A01K 61/00*    (2006.01)
*A01K 67/027*    (2006.01)

(52) U.S. Cl.
USPC .......................... 514/44 A; 119/215; 800/20

(58) Field of Classification Search
None
See application file for complete search history.

(56) References Cited

U.S. PATENT DOCUMENTS 6,458,559 B1 *  10/2002  Shi et al. ...................... 435/69.1
7,265,095 B1 *   9/2007  Secombes et al. .......... 514/44 R

FOREIGN PATENT DOCUMENTS

JP    2005-112726    4/2005

OTHER PUBLICATIONS

Hong et al, Application of QCM DNA biosensor to detect a marine derived pathogenic virus VHSV, 2009, Nanotech Conference and Expo 2009, vol. 2, 197-200.*
Hong, Sung-Rok, et al., "Application of QCM DNA Biosensor to Detect a Marine Derived Pathogenic Virus VHSV", Nanotech Conference & Expo 2009: May 3-7, 2009, vol. 2, pp. 197-200.
Gopinath, S.C., "Antiviral Aptamers", Archives of Virology, 2007, vol. 152, pp. 2137-2157.
Yan, Amy C., et al., "Aptamers: Prospects in Therapeutics and Biomedicine", Frontiers in Bioscience, May 1, 2005, vol. 10, pp. 1802-1827.
Jayasena, Sumedha D., "Aptamers: An Emerging Class of Molecules That Rival Antibodies in Diagnostics", Clinical Chemistry, (1999), vol. 45, No. 9, pp. 1628-1650.

* cited by examiner

*Primary Examiner* — Tracy Vivlemore
*Assistant Examiner* — Kate Poliakova
(74) *Attorney, Agent, or Firm* — McCarter & English

(57) ABSTRACT

A pharmaceutical and a method for preventing and treating VHSV infection in fish with a VHSV-binding aptamer is provided. Also provided are a method for removing VHSV from an area of water and a method and kit for detecting VHSV with high sensitivity using a VHSV-binding aptamer.

13 Claims, 4 Drawing Sheets

Fig. 1

|    | T7 Fw primer binding region | Randomized sequence region | M13 Rv primer binding region | |
|----|----|----|----|----|
| F1 | UAAUACGACUCACUAUAGGGCAGGCAGCGAGUG–AGUUUCG–UUCCCGUA–UAGUAAACUUCUGACGGAAUGU– | | UCCGACCACACGGCGUCCGAGA | (SEQ ID NO: 1) |
| F4 | UAAUACGACUCACUAUAGGGCAGGCAGCGAGUG–AGUUUCG–UUCCCGUA–UAGUAAACUUCUGACGGAAUGU– | | UCCGACCACACGGCGUCCGAGA | (SEQ ID NO: 1) |
| F5 | UAAUACGACUCACUAUAGGGCAGGCAGCGAGUG–AGUUUCG–UUCCCGUA–UAGUAAACUUCUGACGGAAUGU– | | UCCGACCACACGGCGUCCGAGA | (SEQ ID NO: 1) |
| F2 | UAAUACGACUCACUAUAGGGCAGGCAGCGAGUGUGAGCAGCAGUCCAUCAGUCCUGUAUUCCUGACGGACG– | | CCGACCACACGGCGUCCGAGA | (SEQ ID NO: 2) |
| C1 | UAAUACGACUCACUAUAGGGCAGGCAGCGAGUGUGAGCAGCAGUCCAUCAGUAUAUUCCUGUAUAAGGGACG– | | CCGACCACACGGCGUCCGAGA | (SEQ ID NO: 2) |
| F3 | UAAUACGACUCACUAUAGGGCAGGCAGCGAGAAUGAGAAAUGAUUUGUGUUAGGUCUCUAUCGAAAGG– | | GC–CCGACCACACGGCGUCCGAGA | (SEQ ID NO: 3) |
| C8 | UAAUACGACUCACUAUAGGGCAGGCAGCGAGUGA–AUUAGCUGUGAUGAUGAGUGGAAUAAAGACGUGAAGA– | | CCGACCACACGGCGUCCGAGA | (SEQ ID NO: 4) |
| C6 | UAAUACGACUCACUAUAGGGCAGGCAGCGAGUUGAUGG–UGGGGAACUGUGUGGGAUCUGCACAGUUUA– | | CCGACCACACGGCGUCCGAGA | (SEQ ID NO: 5) |
| C5 | UAAUACGACUCACUAUAGGGCAGGCAGCGAGACAAUUG– | CUGGGGUAUUUCACCUUGUAAAAUUGGGCGCU– | CCGACCACACGGCGUCCGAAU | (SEQ ID NO: 6) |
| C2 | UAAUACGACUCACUAUAGGGCAGGCAGCGAGUACAAUUG– | CUGGGUUAUUUCGCCGGUAGUGUGUACCGCU– | CCGACCACACGGCGUCCGAAU | (SEQ ID NO: 7) |
| C10 | UAAUACGACUCACUAUAGGGCAGGCAGCGAGGA–AAUAG– | CUACUGGUAGUGUAGUGUACCGCUGCAUGUGGCCGACCACACGGCGUCCGAA– | | (SEQ ID NO: 8) |
| C7 | UAAUACGACUCACUAUAGGGCAGGCAGCGAGGAGAUGCGUUUCU–UCUUGGU–UCCCUUG– | UGUGGUGGAUGUC–UCCGACCACACGGCGUCCGAGA | | (SEQ ID NO: 9) |
| C4 | UAAUACGACUCACUAUAGGGCAGGCAGCGAGGAGCAGGAGCAGCGAGGUUA–UGAUGGCGCCUUGUGUGUUGCUAGUUUGGA– | A–CCGACCACACGGCGUCCGAGA | | (SEQ ID NO: 10) |
| C3 | UAAUACGACUCACUAUAGGGCAGGCAGCGAGGUUAGGC–UAGUGUGA– | GAUUGUGCAUUAGUUUAGAUUG– | CCGACCACACGGCGUCCGA– | (SEQ ID NO: 11) |
| C9 | UAAUACGACUCACUAUAGGGCAGGCAGCGAGCCAGGCCAGGCGAGCGCCUGGAGCU–UGUUG– | AUUCACACUAGUUGCUGCUCGUGUUCC– | CCGACCACACGGCGUCCGAGA | (SEQ ID NO: 12) |

Fig. 2-1

0.25 mg/ml RNA; HINAE

Blank | Only buffer | buffer + VHSV
buffer + VHSV + F1 | buffer + VHSV + F2 | buffer + VHSV + C6

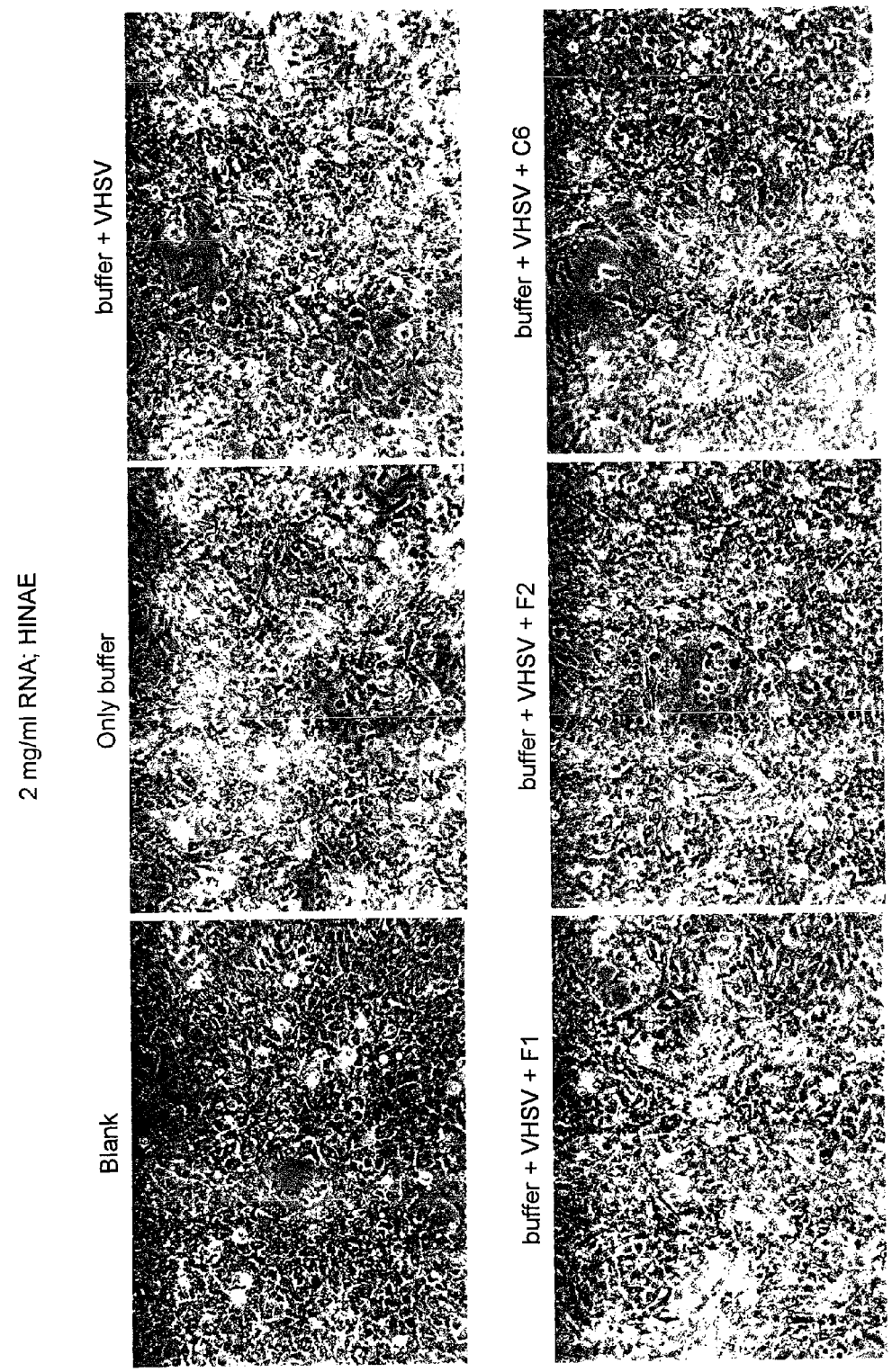

```
                        SEQUENCE LISTING

<160> NUMBER OF SEQ ID NOS: 15

<210> SEQ ID NO 1
<211> LENGTH: 93
<212> TYPE: RNA
<213> ORGANISM: Artificial
<220> FEATURE:
<223> OTHER INFORMATION: RNA aptamer

<400> SEQUENCE: 1
uaauacgacu cacuauaggg ccaggcagcg agugaguuuc guucccguau aguaaacuuc      60
ugacgggaau guuccgacca cacgcguccg aga                                  93

<210> SEQ ID NO 2
<211> LENGTH: 95
<212> TYPE: RNA
<213> ORGANISM: Artificial
<220> FEATURE:
<223> OTHER INFORMATION: RNA aptamer

<400> SEQUENCE: 2
uaauacgacu cacuauaggg ccaggcagcg aguggugcuc ugaguccauc aguauauuuc      60
cuguauaagg ggacgccgac cacacgcguc cgaga                                95

<210> SEQ ID NO 3
<211> LENGTH: 92
<212> TYPE: RNA
<213> ORGANISM: Artificial
<220> FEATURE:
<223> OTHER INFORMATION: RNA aptamer

<400> SEQUENCE: 3
uaauacgacu cacuauaggg ccaggcagcg agaaaugauu uuguguauua ggucucuauc      60
aucugaaagg gcccgaccac acgcguccga ga                                   92

<210> SEQ ID NO 4
<211> LENGTH: 92
<212> TYPE: RNA
<213> ORGANISM: Artificial
<220> FEATURE:
<223> OTHER INFORMATION: RNA aptamer

<400> SEQUENCE: 4
uaauacgacu cacuauaggg ccaggcagcg agugaauuag cugugaugag augguggaau      60
aagacgugaa gaccgaccac acgcguccga ga                                   92

<210> SEQ ID NO 5
<211> LENGTH: 94
<212> TYPE: RNA
<213> ORGANISM: Artificial
<220> FEATURE:
<223> OTHER INFORMATION: RNA aptamer
```

<400> SEQUENCE: 5
uaauacgacu cacuauaggg ccaggcagcg agaguuguga uguugggugg acugugugga    60
uucugcacag uuuaccgacc acacgcgucc gaga                                94

<210> SEQ ID NO 6
<211> LENGTH: 92
<212> TYPE: RNA
<213> ORGANISM: Artificial
<220> FEATURE:
<223> OTHER INFORMATION: RNA aptamer

<400> SEQUENCE: 6
uaauacgacu cacuauaggg ccaggcagcg aggacaauug cuggguauu ucaccuugua     60 aaauugggcg cuccgaccac acgcguccga au                                  92

<210> SEQ ID NO 7
<211> LENGTH: 92
<212> TYPE: RNA
<213> ORGANISM: Artificial
<220> FEATURE:
<223> OTHER INFORMATION: RNA aptamer

<400> SEQUENCE: 7
uaauacgacu cacuauaggg ccaggcagcg aguacaauug cuggguuauu ucgccgugua    60
aaaaugugcg cuccgaccac acgcguccga au                                  92

<210> SEQ ID NO 8
<211> LENGTH: 91
<212> TYPE: RNA
<213> ORGANISM: Artificial
<220> FEATURE:
<223> OTHER INFORMATION: RNA aptamer

<400> SEQUENCE: 8
uaauacgacu cacuauaggg ccaggcagcg aggaaauagc uacugguagg uaguguguac    60
cgcugcaugu ggccgaccac acgcguccga a                                   91

<210> SEQ ID NO 9
<211> LENGTH: 92
<212> TYPE: RNA
<213> ORGANISM: Artificial
<220> FEATURE:
<223> OTHER INFORMATION: RNA aptamer

<400> SEQUENCE: 9
uaauacgacu cacuauaggg ccaggcagcg agaugcguuu cuucuugguu cccuugugug    60
guguggaugu cuccgaccac acgcguccga ga                                  92

<210> SEQ ID NO 10
<211> LENGTH: 92
<212> TYPE: RNA
<213> ORGANISM: Artificial
<220> FEATURE:
<223> OTHER INFORMATION: RNA aptamer

<400> SEQUENCE: 10
uaauacgacu cacuauaggg ccaggcagcg agcuuaagug uuugauggcg cuuguuguuu    60
gcuaguuugg aaccgaccac acgcguccga ga                                  92

<210> SEQ ID NO 11
<211> LENGTH: 90
<212> TYPE: RNA

```
<213> ORGANISM: Artificial
<220> FEATURE:
<223> OTHER INFORMATION: RNA aptamer

<400> SEQUENCE: 11
uaauacgacu cacuauaggg ccaggcagcg agacgguuag gcuaguguga gauugugcau      60
uaguuuagau ugccgaccac acgcguccga                                      90

<210> SEQ ID NO 12
<211> LENGTH: 92
<212> TYPE: RNA
<213> ORGANISM: Artificial
<220> FEATURE:
<223> OTHER INFORMATION: RNA aptamer

<400> SEQUENCE: 12
uaauacgacu cacuauaggg ccaggcagcg aguccuggag cuuguugauu cacuaguugc      60
ugcucguguu ccccgaccac acgcguccga ga                                   92

<210> SEQ ID NO 13
<211> LENGTH: 75
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (16)..(55)
<223> OTHER INFORMATION: n is a, c, g, or t

<400> SEQUENCE: 13
gggccaggca gcgagnnnnn nnnnnnnnnn nnnnnnnnnn nnnnnnnnnn nnnnnccgac      60
cacacgcgtc cgaga                                                      75

<210> SEQ ID NO 14
<211> LENGTH: 32
<212> TYPE: DNA
<213> ORGANISM: Artificial
<220> FEATURE:
<223> OTHER INFORMATION: primer

<400> SEQUENCE: 14
taatacgact cactataggg ccaggcagcg ag                                   32

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tctcggacgc gtgtggtcgg                                                 20
```

APTAMER CAPABLE OF BINDING TO VIRAL HEMORRHAGIC SEPTICEMIA VIRUS

RELATED APPLICATIONS

This application is a national stage application filed under 35 USC §371 of PCT/JP2010/068115, filed Oct. 15, 2010, which claims the benefit of Japanese Patent Application No. 2009-239340, filed Oct. 16, 2009, both of which are incorporated herein, in entirety, by reference.

TECHNICAL FIELD

The present invention relates to a viral hemorrhagic septicemia virus (VHSV)-binding aptamer capable of binding to VHSV, a pharmaceutical composition for treating/preventing VHS, containing the same, and a method for detecting VHSV.

BACKGROUND ART

A viral hemorrhagic septicemia (VHS), which is also called egtved disease, is a viral disease occurring primarily in salmonid fish species as well as in a Japanese flounder, a red sea bream, a black rockfish, and the like. The disease attributable to viral hemorrhagic septicemia virus (VHSV) as a pathogen has been known for a long time as a disease of fishes in a fresh water area system mainly in the European continent; however, in recent years, it has also been reported from fresh water areas in North America and sea water areas in Japan, and the water area in which the disease occurs is gradually expanding.

As symptoms of this disease, there are observed melanic body color, protrusion of the eyes, abdominal swelling, hemorrhage in the eyeball, the branchia, the side of the body, and the base of the fin, and behavioral abnormalities such as swimming inactivity and abnormal swimming. In autopsy findings, congestion, expansion, and fading of the liver, kidney, and spleen and petechial hemorrhage of the skeletal muscle are seen (Non Patent Literature 1).

The disease non-latently infects younger fish more easily and has a high mortality of the younger fish; thus, it can cause heavy damage to the fishing industry, particularly to the culture industry. Therefore, there is an urgent need for the development of a simple detection method of the disease as an important disease to the fishery, and a prophylactic and therapeutic method thereof (Non Patent Literature 2).

However, an effective control method against the disease is not yet known; nowadays, a method is only adopted which involves early detecting affected individuals under a health monitoring program and removing them from the population. But, the disease has a large difference in symptoms between individuals; there exist from individuals having dramatic symptoms and resulting in death to individuals appearing almost normal. As a result, individuals having become latent virus carriers viable despite being infected individuals have a high possibility of evading the monitoring. Thus, the control method includes a problem of expanding/spreading the infection to the surrounding water area via such carriers. It also has a problem that it requires a great deal of labor for the monitoring.

Meanwhile, Patent Literature 1 discloses the invention of a DNA vaccine against VHSV. The DNA vaccine is a DNA vaccine encoding an immunogenic polypeptide of VHSV and is excellent in that it can be administered to intended individuals to stimulate the protective immunity of the individuals against VHS to impart the ability to be protected from VHS to the individuals. Because of being DNA, the vaccine also has the advantage that it is stable under high temperature, can be stored for a long period of time, can be rapidly and easily improved by a genetic method, and enables a reduction in time necessary for the development of the vaccine. However, the DNA vaccine has the disadvantage that it is not immediately effective and its protective effect does not appear until about 2 weeks after the inoculation thereof. In addition, a transgenic fish having recombinant plasmid DNA encoding the antigen also has a problem in terms of safety as an edible fish.

CITATION LIST

Patent Literature

Patent Literature 1
JP Patent Publication (Kokai) No. 2005-112726

Non Patent Literature

Non Patent Literature 1
Specified Disease Diagnosis Manual, Prevention of Epidemics in Fishes (Tokutei Shikkan Shindan Manyuaru, Gyorui Boeki Gijutsusho) Series XXV, 2008, Japan Fisheries Resource Conservation Association
Non Patent Literature 2
Shuzo Egusa (Responsible Editor), A Dictionary of The Science of Fish Diseases, 1982, Kindai Shuppan Co., Ltd.

SUMMARY OF INVENTION

Technical Problem

An object of the present invention is to provide a pharmaceutical and a method capable of preventing and treating VHSV infection, a method for removing VHSV from a specific water area, and a method and a kit for simply detecting VHSV with high sensitivity.

Solution to Problem

As a result of intensive studies for solving the above-described problems, the present inventors have succeeded in the development of an aptamer capable of suppressing VHSV infection.

The "aptamer" is a ligand molecule capable of specifically binding to a target substance. The aptamer can be roughly divided into a nucleic acid aptamer and a peptide aptamer according to the type of the molecule. Each aptamer strongly and specifically binds to a target substance via the three-dimensional conformation of the molecule and specifically suppresses the function of the target substance. The aptamer has a function effect similar to antibody in terms of directly binding to a target substance and being capable of being extracellularly brought into action; however, the aptamer is superior to the antibody in terms of being capable of discriminating between closely related molecules since the aptamer generally has higher specificity and affinity to the target substance than those of the antibody and may have the reduced number of target amino acid residues required for binding compared to that of the antibody. Therefore, it is more useful in discriminating between the subtypes or strains of closely related proteins or microorganisms than antibody. In addition, the aptamer has the advantages that it has lower immunogenicity and toxicity than antibody, can be prepared in a short time of about 3 to 4 weeks, and can also be produced in large quantities by chemical synthesis. The aptamer is technically known; for further information, see, for example, Janasena, Clin. Chem. 45:1628-1650 (1999).

As described above, an aptamer has very useful properties; however, an aptamer has not previously been known which has an infection-suppressing activity against a fish-infecting virus. The present invention is based on the above aptamer and provides the following.

(1) A viral hemorrhagic septicemia virus (VHSV)-binding aptamer having an activity of binding to a VHSV and/or a polypeptide expressed in the virus and suppressing the VHSV infection of a host.

(2) The VHSV-binding aptamer according to (1), wherein VHSV has a genotype of type I.

(3) The VHSV-binding aptamer according to (1) or (2), comprising a base sequence represented by any of SEQ ID NOS: 1 to 12.

(4) A DNA encoding the VHSV-binding aptamer according to any of (1) to (3) above.

(5) An expression vector comprising the DNA according to (4) above in an expressible state.

(6) A transformant obtained by introducing the expression vector according to (5) above into an expression host, or a progeny thereof.

(7) The transformant or progeny thereof according to (6) above, wherein the expression host is a microorganism or a fish.

(8) A method for removing VHSV and/or a polypeptide expressed in the virus, comprising circulating water of a particular water area in a filtration tank comprising the microorganism transformant or progeny thereof according to (7) above and removing VHSV and/or a polypeptide expressed in the virus from the particular water area.

(9) A pharmaceutical composition for treating or preventing viral hemorrhagic septicemia (VHS), comprising the VHSV-binding aptamer according to any of (1) to (3) above or the expression vector according to (5) and a pharmaceutically acceptable carrier.

(10) A method for treating or preventing VHS by administering the pharmaceutical composition according to (9) above to a fish.

(11) A detection method for VHSV and/or a polypeptide expressed in the virus using the VHSV-binding aptamer according to any of (1) to (3) above.

(12) The detection method according to (11), wherein the method uses a surface plasmon resonance measuring method, a quartz crystal microbalance measuring method, a colorimetric method, or a fluorescence method.

(13) A VHSV detection kit for detecting VHSV and/or a polypeptide expressed in the virus, comprising the VHSV-binding aptamer according to any of (1) to (3) above.

BRIEF DESCRIPTION OF DRAWINGS

FIG. 1 is a diagram showing the VHSV-binding RNA aptamers selected by the SELEX method of Example 1.

FIG. 2-1 is a series of photographs showing the suppression of VHSV infection in HINAE cells when 0.25 μg/ml each of VHSV-binding aptamers were used.

FIG. 2-2 is a series of photographs showing the suppression of VHSV infection in HINAE cells when 0.5 μg/ml each of VHSV-binding aptamers were used.

FIG. 2-3 is a series of photographs showing the suppression of VHSV infection in HINAE cells when 2 μg/ml each of VHSV-binding aptamers were used.

DESCRIPTION OF EMBODIMENTS

1. VHSV-Binding Aptamer

Figure 2:
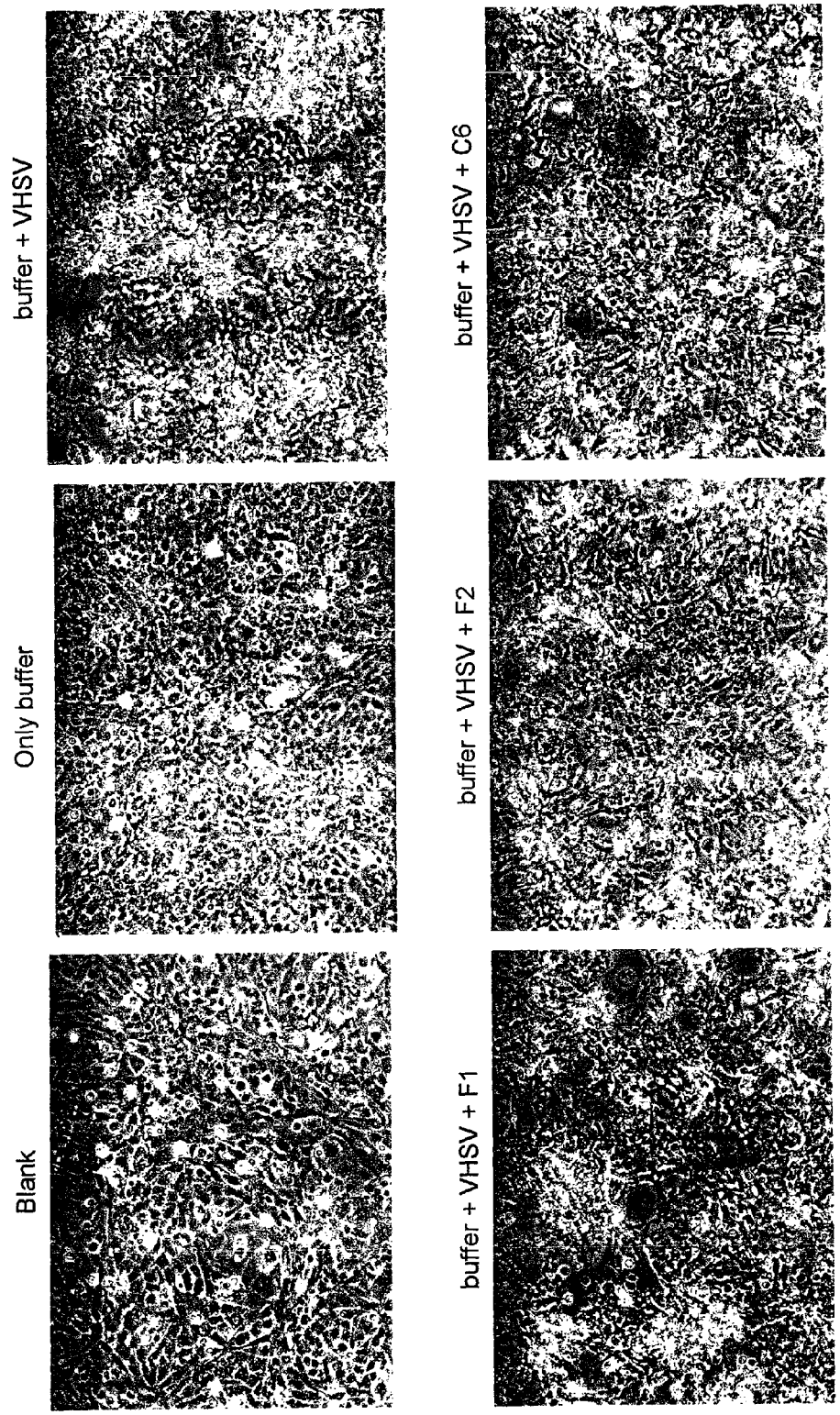

In a first aspect, the present invention is an aptamer having the activity of binding to a viral hemorrhagic septicemia virus (VHSV) and/or a polypeptide expressed in the virus and suppressing the infection thereof to a host. This aptamer is referred to herein as "VHSV-binding aptamer". When the aptamer is an RNA aptamer, it is particularly referred to as "VHSV-binding RNA aptamer".

The "viral hemorrhagic septicemia virus (VHSV)" refers to a virus which is a pathogen for viral hemorrhagic septicemia and is a target of the VHSV-binding aptamer (Byon J Y, et al., Fisheries Science, 72: 906-908). VHSV has been heretofore known to have 4 genotypes: type I (American type), type II (British type), type III (European type), and type IV; however, the genotype of VHSV according to the present invention is not particularly limited. Preferred is type I.

As used herein, the "polypeptide expressed in VHSV" refers to all or part of a VHSV-specific protein encoded in the genome of VHSV. For example, it is the capsid protein of VHSV or a part thereof. The "part" here is a polypeptide which is a fragment of VHSV-specific protein and has an amino acid sequence not losing the specificity of VHSV.

In this aspect, the "host" is a living organism to be infected with VHSV, and generally, fishes, for example, of Salmonidae, Moronidae, Gadidae, Clupeidae, Paralichthyidae, Pleuronectidae, Carangidae, Ammodytidae, Sparidae, and Sebastidae fall thereunder. More specific examples thereof include *Oncorhynchus mykiss, Salmo trutta, Oncorhynchus tshawytscha, Oncorhynchus kisutsh, Dicentrarchus labrax, Gadus morhua, Clupea harengus, Paralichthys olivaceus, Ammodytes personatus, Trachurus japonicus, Pseudocaranx dentex, Sebastes inermis, Pagurus major, Oplegnathus fasciatus*, and *Thunnus albacares*.

As used herein, the "infection to a host" refers to the process from the invasion of VHSV into host cells to the release of a large amount of VHSV from the host cells after proliferation in the cells. As used herein, "suppressing the infection" refers to suppressing the expansion of VHSV infection in the host by inhibiting or suppressing any of the steps of the process of the "infection to a host".

As described above, the aptamer is roughly divided into a nucleic acid aptamer and a peptide aptamer; however, the VHSV-binding aptamer of the present invention is the nucleic acid aptamer. The nucleic acid aptamer refers to an aptamer composed of a nucleic acid. The nucleic acid aptamer typically has a two-dimensional structure or further a three-dimensional structure which a single strand nucleic acid forms via hydrogen bonding or the like, and can strongly and specifically bind to a target substance (for example, a polypeptide) to specifically suppress the bioactivity thereof.

The nucleic acid constructing the VHSV-binding aptamer of the present invention may be DNA, RNA, or a combination thereof. It is preferably an RNA aptamer composed of RNA. This is because RNA generally has flexibility enabling the formation of more conformations than DNA. The aptamer may also include a chemically modified nucleic acid or a pseudo nucleic acid such as PNA (Peptide Nucleic Acid), LNA (registered trademark) (Locked Nucleic Acid)/BNA (Bridge Nucleic Acid), methyl phosphonate DNA, phosphorothioate DNA, or 2'-O-methyl RNA, if necessary.

The VHSV-binding aptamer of the present invention may be labeled, if necessary. The labeling may use any marker for nucleic acid known in the art. Examples thereof include radioisotopes (for example, $^{32}P$, $^{3}H$, and $^{14}C$), DIG, biotin, fluorochromes (for example, FITC, Texas, cy3, cy5, cy7, FAM, HEX, VIC, JOE, Rox, TET, Bodipy493, NBD, and TAMRA), or luminescent materials (for example, acridinium esters). A VHSV-binding aptamer labeled with such a marker can provide a useful tool in detecting the aptamer bound to VHSV in a method for detecting VHSV to be described later.

The VHSV-binding aptamer can be prepared by a method known in the art using VHSV particles or a polypeptide expressed in VHSV as a target molecule. For example, it may be prepared by in vitro selection using an SELEX (systematic evolution of ligands by exponential enrichment) method. The SELEX method is a method which involves selecting RNA molecules bound to a target molecule from an RNA pool consisting of many RNA molecules each having a randomized sequence region and primer-binding regions at both ends thereof; recovering and then amplifying the resultant by a RT-PCR reaction; performing transcription using the resulting cDNA molecules as templates; and using the resultant as an RNA pool at the next round; and repeating this series of cycles over several to several tens of rounds to select RNA having a stronger binding force to the target molecule. The nucleotide sequence length of the randomized sequence region and the primer-binding regions is not limited. Typically, the randomized sequence region is in the range of 20 to 80 base long and the primer-binding regions are each in the range of 15 to 40 base long. To increase specificity for the target molecule, the RNA pool may be mixed with molecules similar to the target molecule, followed by using a pool consisting of RNA molecules having not bound to the molecules. The RNA molecule finally obtained by the above method is used as the VHSV-binding RNA aptamer. The SELEX method is a known method, and the method may specifically be performed according to, for example, Pan et al. (Proc. Natl. Acad. Sci. 1995, U.S.A. 92: 11509-11513).

The nucleotide sequence of the VHSV-binding aptamer is not particularly limited provided that the aptamer is a nucleic acid aptamer capable of binding to VHSV and/or a polypeptide expressed in the virus and suppressing the infection activity of VHSV to a fish. In one embodiment, it is an RNA aptamer comprising the nucleotide sequence represented by any of SEQ ID NOS: 1 to 12 of the present invention. In another embodiment, it is an RNA aptamer consisting of the nucleotide sequence represented by any of SEQ ID NOS: 1 to 12 of the present invention.

The VHSV-binding aptamer can be prepared by any method known in the art. For example, it can be prepared by a chemical synthesis method, based on the nucleotide sequence represented by each of SEQ ID NOS: 1 to 12. The chemical synthesis method is preferable in that the same aptamer can be prepared in large quantities. The production of aptamers by the chemical synthesis method is performed by manufacturers in the life science industry as a contract synthesis business (for example, Invitrogen); thus, it is convenient to use the business. The VHSV-binding aptamer can also be prepared by an in vitro RNA transcription method known in the art (for example, Sambrook, J. et. al., (1989) Molecular Cloning: A Laboratory Manual Second Ed., Cold Spring Harbor Laboratory Press, Cold Spring Harbor, N.Y.) using the DNA encoding a VHSV-binding aptamer to be described later. In addition, the VHSV-binding aptamer may be obtained by using a transformant to be described later to subject it to treatment for inducing the expression of a VHSV-binding aptamer by a technique known in the art and recovering the desired VHSV-binding aptamer from the transformant.

In one embodiment, the VHSV-binding aptamer may be a marker molecule for detecting VHSV and/or a VHSV-specific polypeptide expressed in the virus in a VHSV detection method to be described later. The VHSV-binding aptamer can be a VHSV detection marker having higher sensitivity than VHSV antibodies since it has higher specificity and affinity than the antibodies.

2. DNA Encoding VHSV-Binding Aptamer

A second aspect of the present invention is DNA encoding a VHSV-binding RNA aptamer. Specifically, it is, for example, DNA consisting of a nucleotide sequence in which thymine (T) is substituted for uracil (U) in a nucleotide sequence shown in each of SEQ ID NOS: 1 to 12. Each nucleic acid may be modified with a methyl group or the like, if necessary, and can also include a chemically modified nucleic acid or a pseudo nucleic acid such as PNA (Peptide Nucleic Acid), LNA (registered trademark) (Locked Nucleic Acid), methyl phosphonate DNA, phosphorothioate DNA, or 2'-O-methyl RNA.

The DNA of the present invention can be prepared by performing a reverse transcription reaction using a VHSV-binding RNA aptamer as a template and a primer totally or partly complementary to the 3'-terminal nucleotide sequence of the aptamer. The reverse transcription reaction may be performed using a technique known in the art. See, for example, Sambrook, J. et al., (1989) Molecular Cloning: A Laboratory Manual Second Ed., Cold Spring Harbor Laboratory Press, Cold Spring Harbor, N.Y. The DNA of the present invention can also be produced, for example, by a chemical synthesis method known in the art, based on the information of the RNA aptamer represented by each of SEQ ID NOS: 1 to 12. The production by chemical synthesis is performed by manufacturers in the life science industry as a contract synthesis business (for example, Invitrogen); thus, it is convenient to use the business.

3. VHSV-Binding Aptamer Expression Vector

A third aspect of the present invention is an expression vector containing DNA encoding a VHSV-binding RNA aptamer in a state capable of expression.

"Containing in a state capable of expression" refers to expressibly linking DNA encoding the VHSV-binding RNA aptamer downstream of a promoter in the expression vector.

The expression vector of the present invention may use a plasmid or a phage capable of autonomously proliferating in an expression host. The expression host is a host in which the RNA aptamer encoded in the expression vector can be intracellularly expressed. For example, if the expression vector is a plasmid, pET, pGEX6p, pMAL, pREST, or the like may be used for an *Escherichia coli* host; pUB 110, pTP5, or the like may be used for a *Bacillus subtilis* host; YEp13, YEp24, YCp50, or the like may be used for an yeast host; and pEGFP-1 (Clontech) or the like may be used for a fish hot. If it is a phage, λ phage (λgt11, λZAP, or the like) may be used. In addition, an animal virus such as vaccinia virus or an insect virus vector such as baculovirus may be used.

When a bacterium such as *Escherichia coli* or *Bacillus subtilis* is used as an expression host, the expression vector of the present invention preferably contains an origin of replication for bacteria, a promoter sequence, a ribosomal binding sequence, and a transcription termination sequence in addition to the DNA sequence encoding the VHSV-binding RNA aptamer. The promoter may be any promoter provided that it can exhibit its function in the expression host. A gene encoding a regulatory element controlling the promoter may be contained in the expression vector of the present invention or in a helper vector which is distinct from, but used simultaneously with, the expression vector of the present invention.

When a eukaryotic cell such as yeast, an animal cell, or an insect cell is used as an expression host, a promoter sequence, a cis element such as an enhancer, splicing signals (a donor site, an acceptor site, a branch point, and the like), a poly A addition signal, a selection marker sequence, a ribosomal binding sequence (SD sequence), and the like may be linked to the expression vector of the present invention in addition to the DNA sequence encoding the VHSV-binding RNA aptamer, if necessary.

The method for inserting the DNA encoding the VHSV-binding RNA aptamer into the above vector may use a method known in the art. For example, there is a method which involves digesting a purified product of the DNA with an appropriate restriction enzyme and ligating the resultant into a vector digested with an appropriate restriction enzyme producing corresponding digested ends using of a DNA ligase or the like. For more information, see the method of Sambrook, J. et al., (1989) Molecular Cloning: A Laboratory Manual Second Ed., Cold Spring Harbor Laboratory Press, Cold Spring Harbor, N.Y.

When the expression vector of the present invention is introduced into a desired expression host cell, it can express the VHSV-binding RNA aptamer as long as it is maintained in the cell.

4. Transformant or Progeny Thereof

A fourth aspect of the present invention is a transformant obtained by introducing the expression vector of the above aspect into an expression host, or a progeny thereof.

In this aspect, the "transformant" refers to an expression host transformed by introducing an expression vector containing DNA encoding the VHSV-binding RNA aptamer. The expression host used is not particularly limited provided that it can express the VHSV-binding RNA aptamer encoded in the introduced expression vector. The expression host is generally determined according to the type of the expression vector; thus, one may follow it. Specific preferred examples of the expression host include a bacteria such as *Escherichia coli, Bacillus subtilis*, or *Rhodovulum*; yeast such as *Saccharomyces cerevisiae, Schizosaccharomyces pombe*, or *Pichia pastoris*; an insect cell such as sf9 or sf21; an animal (particularly fish) cell such as a BF-2 cell or a EPC cell; and the fish species capable of being infected with VHSV exemplified in the first aspect.

After being introduced into the expression host, the expression vector of the present invention may be introduced in the genome of the host or may be present in the cell independently of the genome.

The method for introducing the expression vector into bacteria is not particularly limited provided that it is a known method. Examples thereof include a heat shock method, a calcium ion method, and an electroporation method. These techniques are known in the art and described in various references. See, for example, Sambrook, J. et al., (1989) Molecular Cloning: A Laboratory Manual Second Ed., Cold Spring Harbor Laboratory Press, Cold Spring Harbor, N.Y. For the transformation of animal cells, a lipofectin method (PNAS (1989) Vol. 86: 6077), (PNAS (1987) Vol. 84: 7413), an electroporation method, a calcium phosphate method (Virology (1973) Vol. 52: 456-467), a DEAE-dextran method, or the like is preferably used.

In this aspect, the "progeny" of the transformant refers to an offspring via sexual or asexual reproduction of the first generation transformant into which the expression vector of the present invention is introduced, wherein the offspring holds the DNA encoding the VHSV-binding RNA aptamer in a state capable of expression. For example, when the transformant is *Escherichia coli*, a daughter cell resulting from the division of the transformant falls thereunder. The progeny may be of any generation as long as the DNA encoding the VHSV-binding RNA aptamer is passaged therethrough in a state capable of expression.

5. Method for Removing VHSV

A fifth aspect of the present invention is a VHSV removal method which involves circulating water of a particular water area in a filtration tank comprising the microorganism transformant or a progeny thereof among the transformants of the above aspect and removing VHSV from the particular water area.

The "microorganism transformant" refers to the above transformant using a microorganism such as *Escherichia coli* as an expression host. Preferred is the transformant of a microbial species capable of expressing a VHSV-binding RNA aptamer and then extracellularly releasing the aptamer (for example, *Rhodovulum sulfidophilum*). The microorganism transformant to be used may be a transformant derived from an expression host of a microbial species viable in seawater when the filtration tank is used for the seawater or of a microbial species viable in fresh water when the tank is used for the fresh water.

The "filtration tank" is a container or a site containing a filter layer, and is configured to enable water of a particular water area to be circulated through the filtration tank mechanically using a pump or the like or by a natural water stream or a tidal stream. Specific examples of the filtration tank include a filtration tank apparatus or a filtration reservoir. The filter medium used in the filter layer is not particularly limited provided that it is highly permeable and is configured to enable the fixing of the microorganism transformant. Preferred is a filter medium having a large surface area, capable of containing many microorganism transformants in a constant volume. Examples of the filter medium having a large surface area include a fiber mass such as felt or a porous material such as activated carbon, pumice stone, or urethane foam.

The "particular water area" refers to a water area which is within certain boundaries. The water of a particular water area may be any of fresh water, brackish water, and seawater. The area may be an open compartment or a closed compartment. Examples of the closed or semi-closed (partly opened) compartment include a water tank, a paddy, a pond (including a regulation pond), a muddy pond, or a lake. Examples of the open compartment include a preserve installed in a coastal sea area.

The filtration tank described in this invention preferably has the microorganism transformant of the present invention fixed in advance by contacting with the filter layer before installation in a particular water area. Examples of a method for contacting the microorganism transformant with the filter layer include a method which involves immersing the filter layer for several hours to several days in a culture solution in which the microorganism transformant has been cultured. The microorganism transformant fixed on the filter layer releases the VHSV-binding RNA aptamer into the filter layer. Here, water of a particular water area can be circulated through the filtration tank to cause the VHSV-binding RNA aptamer in the filtration tank to bind to VHSV to inactivate its ability to infect a host when VHSV is present in the particular water area. Consequently, VHSV can be removed from the particular water area, resulting in enabling the provision of a water area in which the risk of infection is reduced.

6. Pharmaceutical Composition

A sixth aspect of the present invention is a pharmaceutical composition comprising the VHSV-binding aptamer or the expression vector of the above aspect for treating or preventing viral hemorrhagic septicemia (VHS) and a pharmaceutically acceptable carrier.

In one embodiment, the pharmaceutical composition of the present invention comprises one VHSV-binding aptamer. In another embodiment, the pharmaceutical composition of the present invention may comprise two or more VHSV-binding aptamers within a pharmaceutically acceptable range. For example, the pharmaceutical composition may comprise a combination of any two or more of VHSV-binding RNA aptamers represented by SEQ ID NOS: 1 to 12. This is because when VHSV-binding aptamers bind to different portions of VHSV, the use of a combination of the different VHSV-binding aptamers can more efficiently suppress the infection activity of VHSV.

The "pharmaceutically acceptable carrier" refers to a solvent and/or an additive which can be generally used in the field of formulation technology.

Examples of the solvent include water, ethanol, propylene glycol, ethoxylated isostearyl alcohol, polyoxylated isostearyl alcohol, and polyoxyethylene sorbitan fatty acid esters. These solvents are desirably sterilized, and preferably adjusted to isotonicity with the blood, if necessary.

Examples of the additive include an excipient, a binder, a disintegrant, a filler, an emulsifier, a fluidity increasing/modifying agent, a solubilizer, a buffering agent, a pH adjuster, and a soothing agent.

The formulation of the pharmaceutical composition of the present invention varies according to the administration method, and is properly selected depending on the prescription conditions. The administration method will be described in detail in the next aspect; however, preferred is parenteral administration in this aspect. This is because the VHSV-binding RNA aptamer is generally decomposed in the digestive organs in the case of oral administration. The parenteral administration is preferably intra-tissue administration or mucosal administration. The formulation for a parenteral agent also varies depending on the administration method thereof. For example, an injection is suitably used for intra-tissue administration, and a suspension, an emulsion, a cream, a powder, a paste, a gel, an ointment, a plaster, or the like, for mucosal administration. The shape and size of each of the formulations are not particularly limited provided that they are within those of a corresponding formulation known in the art.

A method known to those of skill in the art can be used to formulate the pharmaceutical composition of the present invention. For example, a method as described in Remington's Pharmaceutical Sciences (Merck Publishing Co., Easton, Pa.) may be used. For example, when it is prepared as an injection, the injection can be produced by a method commonly used in the art after dissolving the VHSV-binding aptamer in a pharmaceutically acceptable solvent, preferably using a diluent made isotonic with the blood. The injection may be blended with common salt, glucose or glycerin in a quantity sufficient to prepare an isotonic solution, and a solubilizer, a buffering agent, a pH adjuster, a soothing agent, and the like which are commonly used. The solution, the emulsion, and the suspension may be prepared by dissolving or suspending predetermined amounts of the VHSV-binding aptamer and a pharmaceutically acceptable salt in the non-toxic aqueous or oily solvent and diluent, further adding a tonicity agent and the like as needed, and sterilizing the resultant.

According to the pharmaceutical composition of the present invention, a therapeutic or prophylactic agent for a host infected with or at risk of infection with viral hemorrhagic septicemia (VHS), that is, a fish can be provided.

7. Therapeutic/Prophylactic Method for VHS

A seventh aspect of the present invention is a method for treating or preventing VHS by administering the pharmaceutical composition of the above aspect to a fish. In this aspect, the "fish" is a fish known to be being infected with or at risk of infection with VHS, preferably one belonging to the fish family exemplified as the host of the first aspect, more preferably a fish species exemplified as the host of the first aspect.

The method for administering the pharmaceutical composition may be a systemic or local administration method. VHSV is considered to enter a fish through the branchia and spread to the whole body (Non Patent Literature 1). Thus, the systemic administration via the blood is preferable. This is because the composition of the present invention can be systemically spread by the blood. Meanwhile, a large number of VHSVs are generally known to be present in the kidney, the spleen, the brain, and the digestive tract. Thus, the administration may be locally carried out to these body parts or organs.

The dosage form of the pharmaceutical composition encompasses any suitable form in which the VHSV-binding aptamer as the active ingredient contained is not inactivated. Examples thereof include parenteral administration such as the above-described intra-tissue administration or mucosal administration. The intra-tissue administration is preferably administration by injection as described above. The injection site is not particularly limited. Examples thereof include intravascular (intravenous, intra-arterial, or the like), subcutaneous, intradermal, intramuscular, intramedullary, intrathecal, intraventricular, intraperitoneal, and intra-intestinal sites. Preferred is an intravascular (intravenous, intra-arterial, or the like), intramuscular, or intraperitoneal site. This is because administration to such sites is relatively low in invasiveness and places a reduced burden on a fish as a subject.

When the pharmaceutical composition of the above aspect is administered, an effective dose thereof capable of exerting a VHS infection-suppressing activity is preferably contained in one dosage unit. As used herein, the "effective dose" refers to a dose of an active ingredient necessary for exerting the function thereof, that is, for the purpose of the present invention, a dose at which the VHSV-binding aptamer can treat or improve VHS, and specifically a dose inhibiting or suppressing the entry of VHSV into cells, their proliferation and/or its extracellular release, imparting resistance to VHS infection to the host, and showing little or no adverse side effects on a living body to be administered. A specific dose can vary depending on the information of the subject, the formulation used, and the administration route. The "information of the subject" includes the progression degree or severity of VHS, the general health, size, weight, sex, drug sensitivity, and tolerance to treatment. When a large dose of the pharmaceutical composition of the present invention is necessary in obtaining a therapeutic or prophylactic effect against VHS infection, it may also be administered in several divided doses for burden relief on a fish.

8. VHSV Detection Method

An eighth aspect of the present invention is a VHSV detection method for detecting VHSV and/or a VHSV-specific polypeptide expressed in the virus using the VHSV-binding aptamer. The detection means is not particularly limited provided that it is a method capable of detecting VHSV. For example, it may use a surface plasmon resonance method, a quartz crystal microbalance method, a turbidimetric method, a colorimetric method, or a fluorescence method.

The "surface plasmon resonance (SPR)" refers to a phenomenon in which the irradiation of a metallic thin film with laser light causes a significant decay in reflected light intensity at a particular incidence angle (resonance angle). The "surface plasmon resonance method (SPR method)" is a method using the phenomenon, and can highly sensitively measure an adsorbate on the metallic thin film surface as a sensor part. According to the present invention, the VHSV-binding aptamer, or VHSV particles or a polypeptide expressed in the virus is fixed on the metallic thin film surface in advance using, for example, a known binding technology such as a biotin/(strept)avidin technology. VHSV or a polypeptide expressed in the virus can be detected by passing a sample on the metallic thin film surface and detecting the difference between adsorbates on the metallic thin film surface before and after passing the sample, produced by the binding between the VHSV-binding aptamer and VHSV or a polypeptide expressed in the virus. A substitution method, an indirect competition method, or the like is known as the SPR method, and any of them may be used. This technology is well-known in the art, and thereon, for example, a method as described in Kazuhiro Nagata and Hiroshi Handa, Real-Time Analysis of Biomolecular Interactions, Springer-Verlag Tokyo, Tokyo, 2000 may be referred to.

The "quartz crystal microbalance method" is a method using a phenomenon in which the adsorption of a substance on the surface of an electrode attached to a quartz crystal decreases the resonant frequency of the quartz crystal according to the mass of the substance. A QCM sensor using this method can quantitatively capture a trace of an adsorbate via the variation of a water resonant frequency. According to the present invention, the presence of VHSV can be quantitatively detected from the variation of the water resonant frequency produced by the binding between the VHSV-binding aptamer and VHSV by fixing the VHSV-binding aptamer or VHSV particles or a polypeptide expressed in the virus on the electrode surface in advance in the same manner as the SPR method and contacting a sample with the electrode surface. This technology is well-known in the art. See, for example, a method as described in J. Christopher Love, L. A. Estroff, J. K. Kriebel, R. G. Nuzzo, G. M. Whitesides (2005) Self-Assembled Monolayers of a Form of Nanotechnology, Chemical Review, 105: 1103-1169; and Toyosaka Moriizumi and Takamichi Nakamoto, (1997) Sensa Kogaku (Sensor Engineering), Shokodo Co., Ltd.

The "turbidimetric method" is a method which involves irradiating a solution with light and optically measuring the decay of the light scattered by a substance floating in the solution or the transmitted light passed through the solution using a colorimeter or the like to measure the amount of the substance in the solution. According to the present invention, VHSV or a polypeptide expressed in the virus in a sample can be quantitatively detected by measuring absorbance before and after adding the VHSV-binding aptamer to the sample. To enhance aggregation due to the binding between the VHSV-binding aptamer and VHSV or a polypeptide expressed in the virus, the VHSV-binding aptamer may also be fixed on a support such as latex in advance.

VHSV or a polypeptide expressed in the virus can also be detected by combined use with an antibody to VHSV or the polypeptide expressed in the virus. For example, a method to which a sandwich method as an ELISA method is applied may be used. In this method, the VHSV-binding aptamer is first fixed on a solid-phase support, followed by adding a sample thereto to bind VHSV present in the sample to the aptamer. Then, after washing out the sample, an anti-VHSV antibody is added for binding to VHSV. After washing, the anti-VHSV antibody can be detected using a suitably labeled secondary antibody to detect VHSV in the sample. The solid-phase support may use an insoluble support having a shape such as a bead, a microplate, a test tube, a stick, or a test piece, consisting of a material such as polystyrene, polycarbonate, polyvinyl toluene, polypropylene, polyethylene, polyvinyl chloride, nylon, polymethacrylate, latex, gelatin, agarose, cellulose, sepharose, glass, metal, a ceramic, or a magnetic body. The fixation of the VHSV-binding aptamer or VHSV or a polypeptide expressed in the virus on the solid-phase support can be achieved by binding according to a known method such as a physical adsorption method, a chemical binding method, or a combination of these methods.

9. VHSV Detection Kit

A ninth aspect of the present invention is a kit for detecting VHSV and/or a polypeptide expressed in the virus, comprising a VHSV detection marker. The kit preferably detects VHSV or the like using VHSV detection method of the above aspect.

The kit may comprise, if necessary, a labeled secondary antibody, a substrate necessary for the detection of the label, a positive control or a negative control, a buffer solution using for diluting or washing a sample, and the like, in addition to the VHSV-binding aptamer. In addition, it may include instructions for the kit.

EXAMPLES

Example 1

Selection of VHSV-Binding Aptamer (Construction of DNA Library and RNA Pool)

First, a DNA library (2.5 mg) was prepared by synthesis under commission to Operon Biotechnology. This DNA library includes about $5 \times 10^{16}$ clones of DNA of a total length of 75 bases having the 40-base randomized nucleotide sequence shown in SEQ ID NO: 13 and a nucleotide sequence corresponding to a forward primer containing T7 promoter and a nucleotide sequence complementary to M13 reverse primer at 5'-side and 3'-side, respectively, thereof.

Subsequently, an RNA pool was constructed from the DNA library using T7 Ribomax™ Express Large Sclae RNA Production System (Promega). The specific procedures were according to the instructions included with the kit.

(SELEX Method)

VHSV-binding aptamers were separated by a SELEX method. The SELEX method was used by somewhat modifying the method of Pan et al. (Proc. Natl. Acad. Sci. U.S.A. 1995, 92: 11509-11513). The specific method is as follows.

(1) Binding Between RNA and VHSV and Recovery of Bound RNA

The RNA pool was dissolved in 50 µl of nuclease-free water contained in a 1.5-ml tube. To make RNAs in linear form, the tube was heated at 90° C. for 3 minutes using a heat block and then immediately placed on ice for 5 minutes. To the tube was added 450 µl of filter-sterilized binding buffer (20 mM TRIS/100 mM NaCl/2.5 mM $MgCl_2$ (pH 7.5)). The RNA sample was passed through a wet filter of a pore size of 0.1 µm through which about 500 µl of binding buffer was passed in advance to remove RNAs bound to the filter.

The resultant filtrate was placed at room temperature, and 50 µl of type I VHSV (distributed by Prof. Mamoru Yoshimizu, Hokkaido University) was added thereto. To bind RNAs to VHSV, it was incubated at 37° C. for 30 to 45 minutes while shaking and then placed on ice for 5 minutes. Thereafter, the sample was filtered with a wet filter of a pore size of 0.1 µm moistened with binding buffer in advance, and each complex of VHSV and RNA (hereinafter referred to as VHSV-RNA) left on the filter was washed with about 500 µl of binding buffer and recovered. Each VHSV-RNA was heated at 90° C. for 5 minutes using a heat block to dissociate VHSV and RNA. To remove VHSV particles, 400 µl of phenol/chloroform/isoamyl alcohol (PCI)-DEPC was added to the tube, vigorously mixed for 10 seconds, and then centrifuged at 13,000 rpm for 10 minutes. The upper layer was recovered and transferred to a new tube. Thereto was added 1 ml of 99% ethanol at −20° C., which was then subjected to ethanol precipitation treatment using Etachinmate (Nippon Gene Co., Ltd.) and 3 M sodium acetate. The recovered RNAs were dissolved in 20 μl of nuclease-free water and preserved at −20° C. These were used as original VHSV-binding aptamers.

(2) cDNA Synthesis by Reverse Transcription Reaction

To select VHSV-binding aptamers more strongly binding to VHSV from the original VHSV-binding aptamers, cDNA providing a template for amplifying the aptamers was synthesized by a reverse transcription reaction. M-MLV system (Promega) was used for the reverse transcription. In a 0.2-ml tube were mixed 10 μl of the recovered RNAs, 1 μl each of a forward primer for the aptamers (AptFw; T7 Fw promoter; SEQ ID NO: 14) and a reverse primer for the aptamers (AptRv; M13 Rv primer; SEQ ID NO: 15), and 1 μl of dNTP. The mixture was heat-mixed at 65° C., transferred onto ice immediately after 5 minutes, and allowed to stand for 5 minutes. Subsequently, 4 μl of 5× first strand buffer, 2 μl of DTT, 0.25 μl of RNase Out, 0.5 μl of MMLV, and 1.25 μl of RNase-free water were added thereto, which was then mixed (total 22 μl), heated at 37° C. for 50 minutes and further at 70° C. for 15 minutes, and then cooled at 4° C. The resultant solution was used for a template cDNA for the original VHSV-binding aptamers.

(3) Amplification of cDNA

The resultant cDNA was amplified by PCR. Using 50 μl of a PCR reaction solution consisting of 36.1 μl of water, 5 μl of 10× buffer for Ex Taq (Takara Bio), 4 μl of dNTP, 1.9 μl each of AptFw and AptRv, 0.6 μl of Ex Taq (Takara Bio), and 0.5 μl of cDNA, PCR was carried out after heating at 95° C. for 1 minute by repeating 10 times the cycle of 95° C. for 1 minute, 50° C. for 15 seconds, and 72° C. for 3 minutes. After the PCR reaction, the product was filled with water to 500 μl, which was then subjected to the treatment of removal of enzyme and the like using an equal amount of PCI and ethanol precipitation, and then dissolved in 30 μl of nuclease-free water to provide a cDNA solution.

(4) Preparation of RNA in Large Amount

To prepare a pool of VHSV-binding RNA aptamers, large amounts of the RNAs were transcribed using the amplified cDNA as a template and T7 Ribomax system (Promega). In each of two 0.2-ml tubes were placed 10 μl of 2× T7 buffer, 5 μl of the cDNA solution, 3 μl of nuclease-free water, and 2 μl of Enzyme X mix (total 20 μl), which was then mixed and incubated at 37° C. for 30 minutes. Subsequently, 5 μl of DNase was added thereto, which was then warmed at 37° C. for 15 minutes. Finally, the samples in the two tubes were collectively filled with nuclease-free water to 400 μl, which was then subjected to the treatment of removal of protein using an equal amount of PCI and ethanol precipitation, and then dissolved in 50 μl of nuclease-free water to use the resultant as second VHSV-binding aptamers. The steps of (1) to (4) were taken as one round.

(5) Repeating of Round

The above round was repeated 12 times. To increase selection stringency, the VHSV concentration used was lowered from $10^4$ nM to 1 nM after each increase in the number of rounds. In rounds 4 to 9, VHSV-RNA was separated from unbound RNA by high-speed centrifugation.

(6) Determination of Nucleotide Sequence of Isolated VHSV-Binding Aptamer

The VHSV-binding aptamers obtained by the above screening rounds were subjected to RT-PCR. As primers were used T7 Fw and M13 Rv primers complementary to primer-binding regions present in both ends of each RNA aptamer. Thereafter, using the T7 primer, the nucleotide sequence of each of the amplified PCR fragments was determined by a sequencer (ABI).

(7) Result

The nucleotide sequences of the VHSV-binding RNA aptamers obtained in this Example are shown in FIG. 1. By the SELEX method, 15 RNA aptamers were obtained. Of these, the 3 clones of F1, F4, and F5 and the 2 clones of F2 and C1 had the same nucleotide sequence; thus, it follows that 12 RNA aptamers were separated.

Example 2

Suppression of VHSV Infection by VHSV-Binding Aptamer

The ability of VHSV-binding aptamers obtained in Example 1 to suppress the infection activity of VHSV was verified.

(1) Cell Culture

Embryo cell line (HINAE) from Japanese flounder (*Paralichthys olivaceus*) (distributed by Prof. Mamoru Yoshimizu, Hokkaido University) was seeded to a monolayer in 3 ml of Leibovitz's L-15 medium (Gibco-BRL) suspended with 10% FBS (JRH Bioscience)/100 IU/ml of penicillin G (Sigma)/100 μg/ml of streptomycin (Gibco-BRL) and cultured at 15° C. for 3 to 4 days. The detailed culture method was according to a method as described in Lua et al., 2008, Antiviral Res. 80(3): 316-323.

(2) Inhibition of VHSV Infection by VHSV-Binding Aptamer

A VHSV infection-inhibiting activity was verified for F1, F2, and C6 among the RNA aptamers obtained in Example 1.

The 3 RNA aptamers were each adjusted to a concentration of 0.2 mg/ml using binding buffer, and after folding, type I VHSV (distributed by Prof. Mamoru Yoshimizu, Hokkaido University) at $10^5$ $TCID_{50}$ was added to 3 ml of each RNA aptamer solution. After incubation at 37° C. for 30 minutes, the solution was added to the HINAE cells prepared in (1) for infection treatment for VHSV. Without anything in the blank, only the buffer was added to a test section for only the buffer, which was then treated with infection in the same way as that for the VHSV test section. HINAE cells after infection treatment were incubated at 15° C., and after 4 to 7 days, the cytopathic effect (CPE) of the VHSV infection was observed under a microscope to examine a VHSV infection-inhibiting activity of each RNA aptamer.

(3) Result

The aptamer-added/VHSV-added test sections (indicated by "buffer+HVSV+F1, F2, or C6" in FIGS. 2-1 to 2-3) to which the three VHSV-binding RNA aptamers (F1, F2, and C6) selected as representatives for the VHSV-binding aptamer of the present invention were added were each low in CPE compared to the aptamer-non-added/VHSV-added test sections (indicated by "buffer+HVSV+F1, F2, or C6" in FIGS. 2-1 to 2-3), confirming that the aptamers inhibited or suppressed VHSV infection. The effect also increased dependent on the concentration of each aptamer. The results demonstrated that the VHSV-binding RNA aptamer of the present invention had the activity of suppressing the VHSV infection of host cells.

INDUSTRIAL APPLICABILITY

The VHSV-binding aptamer of the present invention enables the provision of a molecular-targeted agent capable of suppressing the infection activity of VHSV or a detection marker for highly sensitively detecting VHSV.

The pharmaceutical composition of the present invention enables the prevention of VHSV infection or the treatment of VHS in fishes.

The method for removing VHSV according to the present invention can remove VHSV from a particular water area and enables the provision of a safe water area less infected with VHSV.

The method for detecting VHSV according to the present invention can detect VHSV with high sensitivity.

The VHSV detection kit of the present invention can simply detect VHSV with high sensitivity.

All publications, patents, and patent applications cited in this application are intended to be incorporated herein by reference in their entirety.

The invention claimed is:

1. A viral hemorrhagic septicemia virus (VHSV)-binding aptamer comprising a sequence selected from the group consisting of SEQ ID NOs: 1-12 and having an activity of binding to at least one of a VHSV or a polypeptide expressed by a VHSV and suppressing the VHSV infection of a host.

2. A DNA encoding the VHSV-binding aptamer of claim 1.

3. An expression vector comprising the DNA of claim 2 in an expressible state.

4. A non-human transformant obtained by introducing the expression vector of claim 3 into an expression host or a progeny thereof.

5. The non-human transformant or progeny thereof of claim 4, wherein the expression host is a microorganism or a fish.

6. A method for removing VHSV comprising circulating water of a particular water area in a filtration tank comprising the microorganism transformant or progeny thereof of claim 5 and removing at least one of VHSV or a polypeptide expressed by VHSV from the particular water area.

7. A pharmaceutical composition for treating or preventing viral hemorrhagic septicemia comprising the VHSV-binding aptamer of claim 1 and a pharmaceutically acceptable carrier.

8. A method for treating or preventing viral hemorrhagic septicemia comprising administering to a fish the pharmaceutical composition of claim 7.

9. A detection method for at least one of VHSV or a polypeptide expressed by VHSV comprising binding the VHSV-binding aptamer of claim 1 to the VHSV or the polypeptide.

10. The detection method of claim 9, further comprising detecting the binding of the VHSV or polypeptide and the aptamer by a method selected from a surface plasmon resonance method, a quartz crystal microbalance method, a turbidimetric method, a colorimetric method and a fluorescence method.

11. A VHSV detection kit for detecting at least one of VHSV or a polypeptide expressed by VHSV comprising the VHSV-binding aptamer of claim 1.

12. A pharmaceutical composition for treating or preventing viral hemorrhagic septicemia comprising the expression vector of claim 3 and a pharmaceutically acceptable carrier.

13. A method for treating or preventing viral hemorrhagic septicemia by administering to a fish the pharmaceutical composition of claim 12.

\* \* \* \* \*

UNITED STATES PATENT AND TRADEMARK OFFICE
CERTIFICATE OF CORRECTION

PATENT NO. : 8,580,760 B2  
APPLICATION NO. : 13/502154  
DATED : November 12, 2013  
INVENTOR(S) : Aoki et al.

Page 1 of 1

It is certified that error appears in the above-identified patent and that said Letters Patent is hereby corrected as shown below:

On the Title Page:

In bibliographic description at column 1, after "Inventors: Takashi Aoki, Tokyo (JP); Ikuo Hirono, Tokyo (JP)" and before "Notice," insert:

Item (73) --Assignee: National University Corporation Tokyo University of Marine Science and Technology, Tokyo (JP).--

Signed and Sealed this  
Twenty-fifth Day of November, 2014

Michelle K. Lee  
*Deputy Director of the United States Patent and Trademark Office*